United States Patent [19]

Crum et al.

[11] Patent Number: 4,793,355
[45] Date of Patent: Dec. 27, 1988

[54] APPARATUS FOR PROCESS FOR MAKING BIOMAGNETIC MEASUREMENTS

[75] Inventors: Duane B. Crum, San Diego; Ronald C. Wesley, Cardiff; Richard E. Greenblatt, San Diego; Roberta M. Toussaint, Olivenhain; Eugene C. Hirschkoff, Leucadia, all of Calif.

[73] Assignee: Biomagnetic Technologies, Inc., San Diego, Calif.

[21] Appl. No.: 39,515

[22] Filed: Apr. 17, 1987

[51] Int. Cl.⁴ .............................................. A61B 5/05
[52] U.S. Cl. .................... 128/653; 128/713; 324/201; 324/248
[58] Field of Search ............... 357/5, 68; 307/306; 324/201, 204, 248; 128/731, 733, 630, 640, 644, 653

[56] References Cited

U.S. PATENT DOCUMENTS

| | | | |
|---|---|---|---|
| 3,555,529 | 1/1971 | Brown et al. | 128/653 X |
| 3,557,777 | 1/1971 | Cohen | 128/653 |
| 3,868,565 | 2/1975 | Kuipers | 324/34 R |
| 3,980,076 | 9/1976 | Wikswo, Jr. et al. | 128/713 X |
| 3,983,474 | 9/1976 | Kuipers | 324/43 R |
| 4,004,217 | 1/1977 | Giffard | 324/43 R |
| 4,017,858 | 4/1977 | Kuipers | 343/100 R |
| 4,054,881 | 10/1977 | Raab | 343/112 R |
| 4,079,730 | 3/1978 | Wikswo, Jr. et al. | 324/201 X |
| 4,298,874 | 11/1981 | Kuipers | 343/112 R |
| 4,314,251 | 2/1982 | Raab | 343/112 R |
| 4,328,548 | 5/1982 | Crow | 364/449 |
| 4,328,809 | 5/1982 | Hirschowitz et al. | 128/653 |
| 4,346,384 | 8/1982 | Raab | 343/112 R |
| 4,386,361 | 5/1983 | Simmonds | 357/5 |
| 4,389,612 | 6/1983 | Simmonds | 324/248 |
| 4,403,189 | 9/1983 | Simmonds | 324/248 |
| 4,588,947 | 5/1986 | Ketchen | 307/306 X |
| 4,690,149 | 9/1987 | Ko | 128/653 |
| 4,700,135 | 10/1987 | Hoenig | 324/248 |

OTHER PUBLICATIONS

Introduction to Biomagnetic Measurements and Instruments, Biomagnetic Technologies, Inc., 1984-85.
3Space User's Manual, Polhemus Navigation Sciences Div., Jan. 1985.

Primary Examiner—Lloyd L. King
Attorney, Agent, or Firm—Gregory O. Garmong

[57] ABSTRACT

Apparatus for making biomagnetic measurements includes a biomagnetometer for measuring magnetic fields produced by the body and an electromagnetic location measurement and recording system for automatically determining the location of the portion of the body from which the magnetic signals are being gathered. The electromagnetic location recording system permits establishing a real time body frame of reference with respect to the biomagnetometer, so that biomagnetic signals can be correlated directly with body location and structure. The electromagnetic location recording system may be operated continuously at radiation wavelengths which do not interfere with the taking of data, or intermittently with the taking of biomagnetic data, to avoid interference with the measured values of the biomagnetic data. The elements of the electromagnetic location recording system have substantially no residual magnetism when the location recording system is not operating, as the biomagnetic signals are typically so small that even normal residual magnetism might be erroneously recorded as a biomagnetic signal.

24 Claims, 3 Drawing Sheets

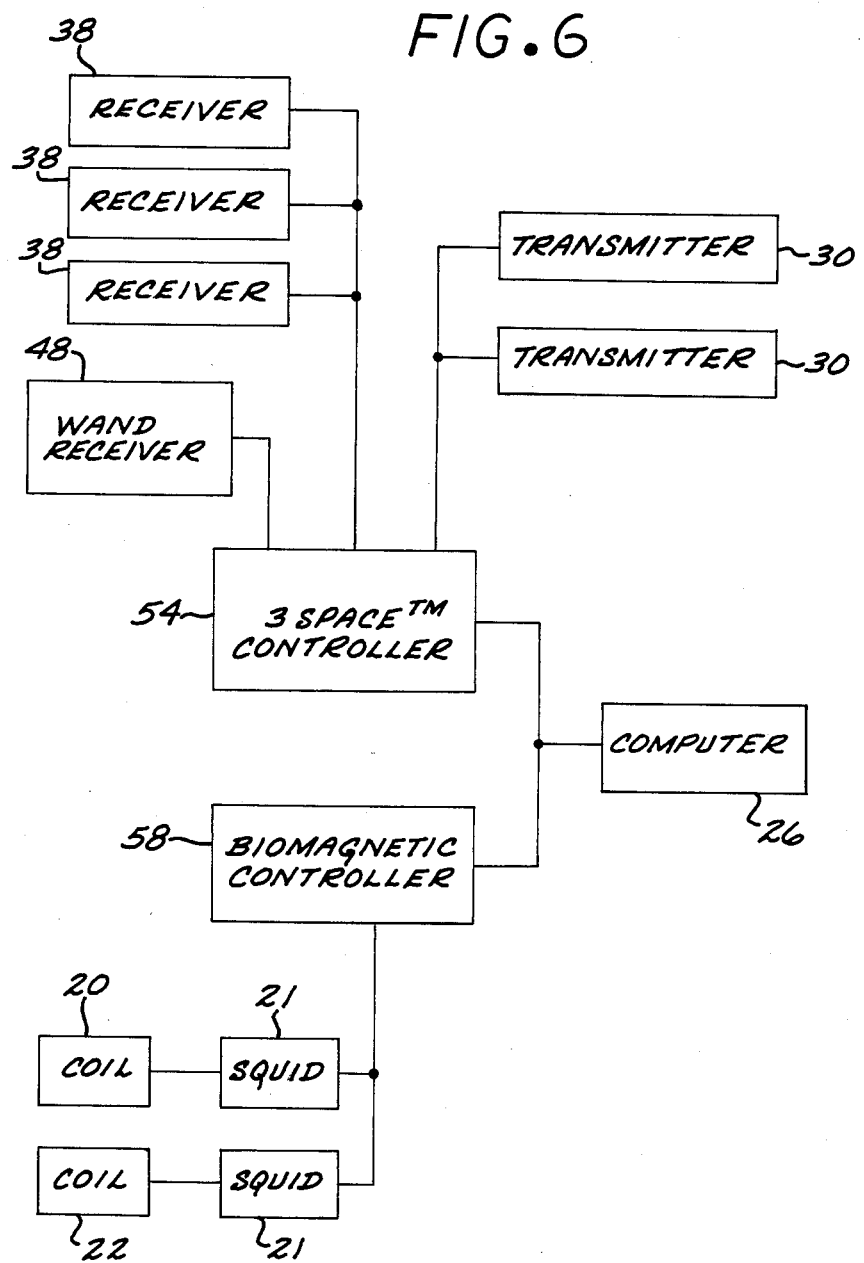

APPARATUS FOR PROCESS FOR MAKING BIOMAGNETIC MEASUREMENTS

BACKGROUND OF THE INVENTION

This invention relates to medical diagnostic instruments, specifically such instruments for making measurements of magnetic fields in the human body, and, more specifically, to instruments wherein the location of the portion of the body being measured may be correlated directly with the biomagnetic measurements.

The human body produces various kinds of energy that may be used to monitor the status and health of the body. Perhaps the best known of these types of energy is heat. Most healthy persons have a body temperature of about 98.6° F. A measured body temperature that is significantly higher usually indicates the presence of an infection of other deviation from normal good health. A simple medical instrument, the clinical thermometer, has long been available to measure body temperature.

Over 100 years ago, medical researchers learned that the body also produces electrical signals. Doctors today can recognize certain patterns of electrical signals that are indicative of good health, and other patterns that indicate disease or abnormality. The best known types of electrical signals are those from the heart and from the brain, and instruments have been developed that measure such signals. The electrocardiograph measures electrical signals associated with the operation of the heart, and the electroencephalograph measures the electrical signals associated with the brain. Such instruments have now become relatively common, and most hospitals have facilities wherein the electrical signals from the bodies of patients can be measured to determine certain types of possible disease or abnormality.

More recently, medical researchers have discovered that the body produces magnetic fields of a type completely different than the other types of energy emitted from the body. The research on correlating magnetic fields with various states of health, disease and abnormality is underway, but sufficient information is available to demonstrate that certain emitted magnetic fields are associated with conditions such as epilepsy and Alzheimer's disease. Present medical studies are investigating the nature of the normal and abnormal magnetic fields of the brain, and seeking to correlate those fields with the precise location in the brain from which they emanate. If it were known that a particular abnormality, such as Alzheimer's disease, were associated with an abnormal magnetic field produced at a particular location in the brain, then it might be possible to detect the abnormality at an early stage, while it was treatable, and then apply other medical knowledge to treat that precise portion of the brain. Magnetic studies of the brain therefore offer the potential for understanding and treating some of the most crippling diseases and conditions known.

The biomagnetometer is an instrument that has been developed for measuring magnetic fields produced by the body, particularly the brain. The biomagnetometer is a larger, more complex instrument than the medical instruments mentioned earlier, primarily because the magnetic fields produced by the body are very small and difficult to measure. Typically, the strength of the magnetic field produced by the brain is about 0.00000001 Gauss. By comparison, the strength of the earth's magnetic field is about 0.5 Gauss, or over a million times larger than the strength of the magnetic field of the brain. Most electrical equipment also produces magnetic fields, in many cases much larger than that of the earth. It is apparent that, unless special precautions are taken, it is not possible to make magnetic measurements of the human body because the external influences such as the earth's magnetism and nearby apparatus can completely mask the magnetic fields from the body.

The biomagnetometer is a medical instrument that includes a very sensitive detector of magnetic signals. The currently most widely used detector is a Superconducting QUantum Interference Device or SQUID, which is sufficiently sensitive to detect magnetic signals produced by the brain. (See, for example, U.S. Pat. Nos. 4,386,361 and 4,403,189, whose disclosures are incorporated by reference, for descriptions of two types of SQUIDs.) This detector and its associated equipment require special operating conditions such as a cryogenic dewar, and cannot be placed into the body or attached directly to the surface of the body.

The present biomagnetometer therefore provides a table upon which the patient lies, and a structure which places the SQUID in proximity with the head of the patient, as about 8 inches away. Special electronics is provided to filter out external effects such as the earth's magnetic field and the magnetic fields of nearby electrical instruments. (For a description of such a device, see U.S. Pat. Nos. 3,980,076 and 4,079,730, whose disclosures are herein incorporated by reference.) The patient and detector can also be placed into a magnetically quiet enclosure that shields the patient and the detector from the external magnetic fields. (For a description of such an enclosure, see U.S. Pat. No. 3,557,777, whose disclosure is herein incorporated by reference.) With these special precautions, medical researchers and doctors can now make accurate, reliable measurements of the magnetic fields produced by the brain, and are studying the relationship of these fields with diseases and abnormalities.

As discussed above, it is particularly important to be able to correlate the measured biomagnetic field with the exact location in the brain from which the field emanates. It is well established that certain physically identifiable locations in the brain are responsible for specific types of activities and functions. It is therefore important to correlate the measured biomagnetic field with the particular location in the brain which produces the field. Such a correlation is important to understanding the mechanism by which disease and disorder arise, and also to the treatment of the problem.

At the present time, there is no automatic, reliable, and accurate method for correlating the measured biomagnetic field with the precise location from which it emanates, within the head of the patient. The person whose biomagnetic fields are being measured may be asked to keep his head motionless during the course of the measurements, and his head position determined by physical measurements, photographs, or X-rays before or after the magnetic measurements. While this approach may have value in a few situations, in others it is nearly useless. The person may be asked to keep his head stationary to within 1 millimeter or so for several hours. For example, if the disease under study is epilepsy, many consecutive hours of observation may be required before an attack occurs. Movements of the person's head during the taking of data can invalidate any attempted correlation of the data with head position. That some data is invalid may be hard to detect, since the head movement may be brief and the patient may return his head to nearly the same initial location.

Alternatively, the person's head may be constrained to a relatively fixed position with a restraint system such as a frame and straps, and then photographed, X-rayed or physically measured at the beginning and end of the biomagnetic measurement session. This approach is likely to be uncomfortable for the patient, and may result in spurious signals that interfere with the biomagnetic measurements of interest. Even if the patient can keep his head stationary, the accuracy of correlation of the head position and the biomagnetic signal is not sufficiently great for some applications.

There is therefore a need for an apparatus and method for measuring biomagnetic fields and correlating those fields with the position of the patient's body, in a more exact manner than has been heretofore achieved. Preferably, such an approach would operate automatically to record head position in real time, so that the measured biomagnetic field could be correlated with the body position at the moment of measurement. Further, the measurement approach must not produce magnetic fields that are so large as to interfere with the principal function of the instrument, the measurement of very weak biomagnetic fields. This last requirement is particularly demanding, as most measurement devices having any electrical current flow produce magnetic fields of a magnitude that can interfere with the biomagnetic measurements. The present invention fulfills the need for such a biomagnetic measuring system, and further provides related advantages.

SUMMARY OF THE INVENTION

The present invention is embodied in an apparatus and process for making biomagnetic measurements of the human body, wherein the location of the portion of the body from which measurements are taken is determined and recorded with the biomagnetic data itself. The biomagnetic data is thus correlated with the exact location of it source within the body, even when the patient moves during the course of a measurement session. The body location data is used to construct an internal coordinate system of the portion from which biomagnetic data is taken, so that the exact interior source of the data is determined. The body location measurement system is noncontacting in the sense that the movement of the patient is not restrained, and is comfortable for the patient to use during a protracted session.

In accordance with the invention, apparatus for making magnetic measurements of the human body comprises biomagnetometer means including a sensor for measuring magnetic fields arising from a selected portion of the body; and means for recording in real time the location of the selected portion of the body from which biomagnetic fields are measured, said means for recording including electromagnetic means for sensing the location of the selected portion of the body using an electromagnetic signal. A related process for obtaining biomagnetic data from the human body and correlating that data to the structure of the body comprises the steps of supplying apparatus as just described, operating said means for recording to record the location of the selected portion of the body; taking data from said biomagnetometer means; and recording the biomagnetic data with the information on the location of the selected portion of the body, whereby the biomagnetic data is correlated with the location of the body.

The biomagnetometer means is preferably a unit having a superconducting quantum interference device (SQUID) operating at cryogenic temperature for making sensitive measurements of the magnetic fields produced by the human brain, although the magnetic fields produced by other parts of the body can also be studied. The patient rests with his head and body on a table in the apparatus, with at least one and possible two dewars containing SQUIDs movably positioned about 12 inches or so from his head. Magnetic fields produced by the brain are picked up by magnetic sensing coils, detected by the SQUIDs, and recorded in a computer, after the necessary filtration, amplification, and signal processing of the magnetic field signal. The SQUIDs are movable relative to the body of the person so that a map of the origins of the magnetic fields may be prepared.

The biomagnetic measurements may be accomplished in a shielded or unshielded environment, but the shielded environment is preferred. The magnetic fields of the brain are typically less than 1/10,000,000 as great as the earth's magnetic field and the magnetic fields of laboratory and medical apparatus normally found near to such a biomagnetometer apparatus. The effects of these external fields can overwhelm those of the brain and make their measurement impossible, when the fields due to the brain are to be measured by an external instrument, unless measures are taken to nullify their influence. Electronic signal processing can be used to enhance the magnetic field signal of the brain relative to the environmental magnetic fields. Alternatively, the patient and SQUID sensor can be placed into a magnetically quiet enclosure which shields the patient and sensor from the external effects.

The exact location of the head of the person is measured and recorded in a rapid, automatic fashion substantially simultaneously with the recording of the biomagnetic data, so that the location of the head, and the interior regions of the brain, can be determined from the location information obtained just before and just after each bit of biomagnetic data. The location of the head is preferably measured using an electromagnetic locating signal transmitted between the body of the person and the apparatus. This locating signal is electromagnetic in nature, but is to be clearly distinguished from the magnetic field generated by the body itself and measured by the biomagnetometer. The locating signal is generated by a transmitter and received by a receiver which are provided as part of the apparatus. In one embodiment of such an apparatus, one of a transmitter or receiver is mounted on the head of the person, and the other is mounted stationary on the apparatus. In another embodiment, the transmitter is mounted separately from the head and apparatus, and receivers are mounted on both the head and the apparatus. Normally, the receiver is mounted on the head and the transmitter on the apparatus, and for ease of description the following discussion will follow that convention.

In this preferred approach, the transmitter includes three coils orthogonal to each other, through which a current is passed to generate a magnetic loading signal. The signal is received by the receiver, which also includes three coils orthogonal to each other, and converts the received signal to an electrical current. The resulting information permits the determination of the position and relative orientation of the receiver to the transmitter in six axes. Most preferably multiple receivers, as three receivers, are used to reduce measurement errors inherent in the system, obtain redundant data, and account for shape variations and body flexibility during measurements. The general approach for obtaining location and orientation data is known for use in certain other applications such as aircraft landing systems, see, for example, U.S. Pat. No. 3,868,565, whose disclosure is herein incorporated by reference. However, the apparatus used in other applications cannot be used for measurements of the location of the body in conjunction with biomagnetic measurements, because the magnetic fields produced by conventional electromagnetic locating devices overwhelm the biomagnetic signals and because of specific problems associated with measurements of a portion of the body itself.

In one embodiment, the locating device is operated intermittently with the taking of biomagnetic data. That is, the biomagnetic data is taken for a period of time, and then data taking is discontinued. The electromagnetic location recording means is activated for a period sufficiently long to obtain the necessary locating signal information, and then turned off. Taking of biomagnetic data then resumes. The positioning signal information can be obtained in about 1/10 second or less, and therefore the interruption to the biomagnetic data is hardly perceivable. Yet in that short interruption, suffficient locating data is obtained so that the location of the source of the data relative to the sensor is determined with an accuracy of about 1-3 millimeters.

In another embodiment, the locating device is operated continuously, even while biomagnetic data is taken. In this continuous operation embodiment, the transmitter of the locating device is operated at a frequency much greater than the frequencies of the magnetic signals of interest, so that any transmitter signal picked up by the biomagnetometer may be readily filtered from the biomagnetic signal.

The transmitters and receivers previously available were not suitable for use in the location recording means, as they exhibited a residual magnetism after being turned off during the taking of biomagnetic data. The residual magnetism is sufficiently great to interfere with the measurements of the biomagnetic fields. The design of the transmitters and receivers was therefore selected to reduce the residual magnetism to an acceptably low level. Specifically, a sufficient reduction in residual magnetism can be accomplished by removing the ferromagnetic cores used in the standard commercial antenna loops, and by using a potting compound for the transmitter and receivers that has no residual magnetism. The elimination of the ferromagnetic cores reduces the power and range of the electromagnetic location recording system, but such capabilities are not needed in the present system, wherein the separation of the transmitter and receivers is never more than about 12-24 inches.

The mounting of the transmitter on the apparatus poses no problem, but the mounting of the receivers on the body does. The ultimate locating information required is not simply the location of the receivers with respect to the transmitter, but instead is the location of the interior portions of the head, specifically the portions of the brain, with respect to the transmitter. An approach for determining the location of the brain with respect to the receivers is therefore required. That is, the problem posed by the need to correlate biomagnetic measurements with their source is more complex than that of an aircraft landing system, one prior application of electromagnetic positioning systems, in that the relative location of interior objects is required. The comparable requirement for a landing system would be that not just the location of the airplane, but the location of each passenger therein, was required by the landing system.

The present invention further provides for mounting the receivers to the head in a comfortable and acceptable manner, and then electromagnetically measuring the locations of identifiable features of the head with respect to the receivers. The location of the SQUID sensor is also measured electromagnetically. In this way, the relative locations of the head with respect to the transmitter and the receivers, the receivers with respect to the transmitter, and the sensor with respect to the transmitter are all determined electromagnetically and stored in the computer. From this information gathered during the data taking procedure, the exact relative locations of the features of the head can be determined and correlated to the biomagnetic data to obtain a map of the biomagnetic activity of the brain to within about 2-3 millimeter accuracy.

The location of objects such as portions of the head are determined using an electromagnetic wand receiver that may be touched to objects and activated selectively to record their position relative to the transmitter. This wand receiver is in the nature of a elongated wand that may be moved about, and contains a three-axis coil receiver of the same general type as those of the stationary receivers. The locations of objects of interest are recorded prior to the commencement of data taking, and can also be recorded during extended pauses in data taking or at the end of the data taking session as a cross check, or if there is some reason to suspect that relative movement has occurred.

The location of the magnetic sensing coils is measured by touching the wand receiver to reference marks on the dewar in which the coils are immersed, and X-raying the deward to ascertain the exact location of the coils therein. The location of the head is determined by touching the wand receiver to reference points on the head. Preferably, the preauricular points on either side of the head and the nasion are used as reference points. By establishing their locations, an internal head coordinate system within the head of the patient can be defined, and measurements of brain magnetic activity correlated to that coordinate system. Other reference points on the head can also be located using the wand receiver, if they can be associated with reference marks or distinctive features of the head. Finally, the exact shape of the head is determined by traversing the probe receiver over the external surface of the head, while operating it in a continuous measurement mode.

It has been found particularly convenient and effective to mount the receivers to the head of the patient using an elastic headband. The receivers are removably affixed to the headband, as with Velcro, and then the headband is slipped over the head of the patient. This arrangement is comfortable for the patient, even during extended data taking sessions, and yields accurate locational data if the patient takes reasonable care to hold steady during the session. If necessary, the receivers can be affixed by other means, as with the physiological adhesives often used to attach medical sensors to the body.

Thus, in one embodiment, apparatus for making magnetic measurements of the human body comprises a biomagnetometer including a sensor for measuring magnetic fields arising from a selected portion of the body; an electromagnetic transmitter adjacent the body being measured, the transmitter having substantially no residual magnetism when no electric current is flowing therethrough; at least one electromagnetic receiver mounted on the selected part of the body, the electromagnetic receiver having substantially no residual magnetism when no electric current is flowing therethrough; an electromagnetic wand receiver that may be touched to points on the selected portion of the body to indicate the location of such points relative to the electromagnetic transmitter; and computer means for controlling and recording the positions of the receivers and the probe receiver, for taking data from the biomagnetometer, and for controlling the transmitter to transmit electromagnetic signals. A related process for obtaining biomagnetic data comprises the steps of supplying the apparatus just described, operating the transmitter and the receivers and the probe receiver to record the location of the selected portion of the body; taking data from the biomagnetometer; and recording in the computer means the biomagnetic data with the information on the location of the selected portion of the body, whereby the biomagnetic data may be correlated with the location of the body.

It will now be appreciated that the apparatus and process of the invention represent a significant advance in the art of making medical measurements of the human body, whereby biomagnetic measurements may be made and correlated with high accuracy to the exact region of the body which produces them. The approach is automated, so that the biomagnetic data is automatically correlated with the locational information. Other features and advantates of the invention will be apparent from the following more detailed description, taken in conjunction with the accompanying drawings, which description illustrates, by way of example, the principles of the invention.

BRIEF DESCRIPTION OF THE DRAWINGS

FIG. 5 is a perspective view of a wand receiver;

FIG. 6 is a block diagram of the apparatus of FIG. 1;

DETAILED DESCRIPTION OF THE PREFERRED EMBODIMENT

Figure 1:
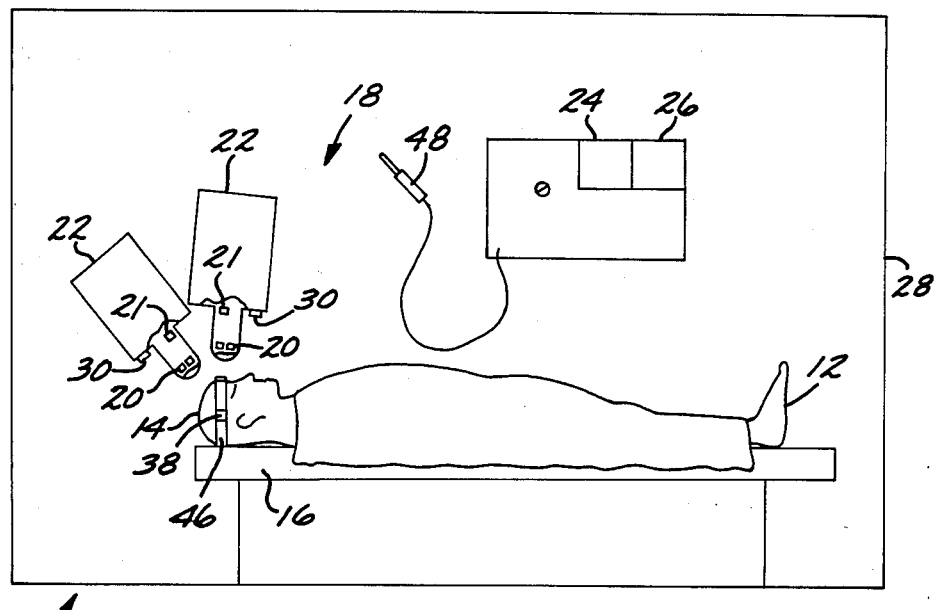
FIG. 1 is a side elevational view of an apparatus in accordance with the invention, with a patient in position for measurement.

As illustrated in FIG. 1, the present invention is preferably embodied in an apparatus 10 for obtaining biomagnetic data from the body 12 of a human patient. More specifically, the data is normally obtained from biomagnetic sources within the head 14 of the person. The body 12 is placed upon a table 16 in proximity with a biomagnetometer 18. The biomagnetometer 18 includes a plurality of magnetic sensing coils 20 for measuring small magnetic fields. The output signal of each magnetic sensing coil 20 is detected by a detector, preferably a superconducting quantum interference device 21 (SQUID). Both the magnetic sensing coil 20 and the SQUID 21 are maintained at a cryogenic operating temperature within a liquid helium dewar 22. In the preferred practice, and as illustrated, two dewars 22 are used, with about 7 SQUIDs in each dewar. This apparatus 10 gives good spatial resolution of the biomagnetic signals for reconstruction of their origin. The present invention is not so limited, and may be used in conjunction with biomagnetometers having one, three, or more dewars 22.

The magnetic signals from the brain are picked up by the magnetic sensing coils 20 in the dewars 22, and the signals are detected by the SQUIDs 21. The SQUIDs 21 detect the magnetic field values as electrical currents that are processed in an electronics system 24 and stored in a computer 26 as a function of time. The sensors 20 and the body 12 of the patient are preferably, but not necessarily, enclosed within an enclosure 28 that shields the apparatus and magnetic field source from external magnetic influences. By screening off the external influences, the amount of signal processing and filtering required to obtain a meaningful indication of the biomagnetic field is reduced.

Figure 3:
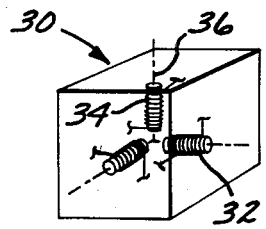
FIG. 3 is a perspective view of the interior of a transmitter

A means for recording the location of the head 14 is provided in the apparatus 10. The means includes a means for sensing the position of tbe head 14 electromagnetically. Preferably, there is provided a transmitter 30 mounted stationary on each of the dewars 22 of the biomagnetometer 18. The transmitter 30, schematically illustrated in FIG. 3, comprises three orthogonal coils 32 of electrically conducting wire that serve as antennas. The coils 32 are wrapped on nonconducting cores 34. There is no ferromagnetic core, as is often provided in loop antennas. It has been found that ferromagnetic cores have a residual magnetism (or remnance) which is large enough to be detected by the magnetic sensing coils 20. This residual magnetism, present even when there is no current flowing through the coils 32, can overshadow the magnetic field of the head 14. While it may be possible to filter or otherwise remove the effects of this residual magnetism, it has been found preferable to eliminate the effect altogether. Elimination of the ferromagnetic core reduces the signal strength of the antennas, but it has been found that the signal strength without the ferromagnetic core is sufficient for use in conjunction with the biomagnetometer 18.

It is common practice to encapsulate, or "pot", the coils 32 in a hard, nonconducting material to electrically insulate the coils and protect them from damage. Potting compounds are typically filled epoxy materials, comprising a curable epoxy mixed with a filler for added strength and hardness. The coils 32 mounted to a support structure 36 are placed into a container with the lead wires extending outside the container, and the liquid mixture of the potting compound is poured around the coils and allowed to harden. The transmitter is then relatively rugged and can be readily handled for mounting and use.

Typical fillers for the epoxy of the potting compound are glass powders. It has now been found that such fillers can have a sufficiently high residual magnetism, even when no current is flowing through the coils 32, to interfere with the taking of biomagnetic data. A filler having substantially no residual magnetism has therefore been substituted for the conventional filler materials. The preferred filler material for the potting compound used in conjunction with the present invention is quartz. To prepare the potting compound for use with the transmitter 30, enough quartz powder to give the desired hardness of the final product is mixed with a magnetically clean epoxy resin. This epoxy/quartz mixture is pourable and hardens in about 2 hours at ambient temperature. This potting compound is used to pot or encapsulate the transmitter 30. The use of this special potting compound and the use of no ferromagnetic core results in substantially zero residual magnetism in the transmitter 30 when no current is flowing through the coils 32.

Figure 4:
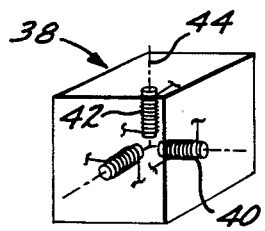
FIG. 4 is a perspective view of the interior of a receiver.

At least one, and most preferably three, receivers 38 are mounted on the portion of the body 12 of the patient from which biomagnetic data is to be taken, here illustrated as the head 14. These receivers 38 receive electromagnetic signals from the transmitter 30, to permit determination of the location of the receivers 38 with respect to the transmitter 30, in a manner to be subsequently described. As illustrated in FIG. 4, these receivers are constructed of three orthogonal coils 40 of electrically conducting wire wound on nonconducting cores 42 and supported by a support structure 44, in a manner generally similar to the construction of the transmitter 30. As in the case of the transmitter 30, it has been found that receivers 38 constructed in the conventional manner have a residual magnetism that is sufficiently large to interfere with the taking of biomagnetic data. The receivers 38 are therefore constructed with the modifications discussed previously for the transmitter 30. That is, there is no ferromagnetic core in the receivers 38, and the receivers 38 are potted in the potting compound having substantially no residual magnetism. Consequently, when there is no electrical current flowing through the coils 40, there is substantially no residual magnetism of the receivers 38.

Figure 2:
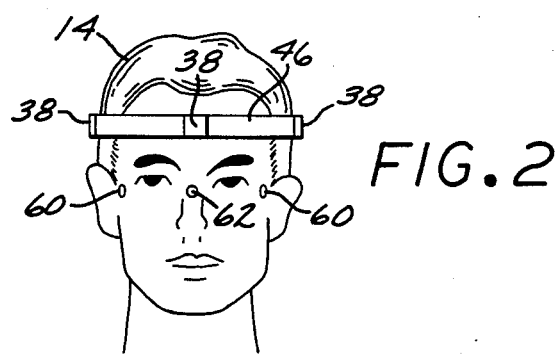
FIG. 2 is a full face view of a person wearing a headband with receivers attached, and indicating reference points.

As illustrated in FIG. 2, the receivers 38 are mounted to the head 14 of the patient on an elastic rubber headband 46. Alternatively, the receivers 38 may be fixed to the head with an adhesive. This headband 46 is comfortable for the patient to wear, an important feature of a system wherein the patient may be required to remain still for up to four hours for the taking of data. The headband 46 is adjusted to a snug fit on the head 14, so that the receivers 38 do not move relative to the head 14 when the patient remains relatively quiet. Of course, if the patient were to engage in strenuous activity, the headband and receivers might move somewhat relative to the head, but this type of activity does not occur during use of the apparatus 10.

In the preferred embodiment just described, the receivers are placed on the head and the transmitters on the dewar. The transmitters and receivers ultimately yield data on the relative location of the two, so that, alternatively, the receivers may be placed on the dewar and the transmitters on the head. The transmitters could also be placed apart from either the head or the dewar, with receivers on both the head and dewar.

Figure 8:
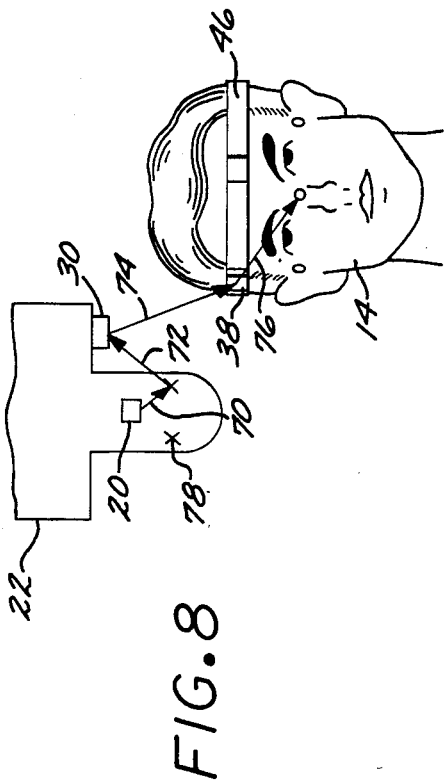
FIG. 8 is an illustration of the frames of reference pertinent to the determination of positions.

The use of the transmitter 30 and the receivers 38 permit the six axis location of each of the receivers 38 to be determined with respect to the transmitter 30. However, the actual correlation of interest is the location of the head 14 with respect to the transmitter 30, and ultimately with respect to the magnetic sensing coils 20. FIG. 8 depicts the reference frames of interest. One cannot be certain that the headband 46 will be placed on the head of any one patient the same way each time data is taken. Also, the heads of different persons have different shapes. The location of the head 14 with respect to the receivers 38, the transmitters 30 and the magnetic sensing coils 20 must therefore be established accurately.

The location of the head 14 is established through the use of a wand receiver 48, illustrated in FIG. 5. The wand receiver 48 is an electromagnetic receiver of the same general capabilities as the receivers 38, except that it is hand held by the person supervising the taking of biomagnetic data from the patient. Three orthogonal coils are mounted in the tip of a wand 50 portion of the wand receiver 48. The wand is touched to a point whose location is to be determined with respect to the transmitter 30, and in this position the receiving circuitry is activated to record the position of the coils of the wand receiver.

A conventional construction may be used for the wand receiver 48, inasmuch as the wand receiver 48 is used when biomagnetic data is not being taken, and is removed from the vicinity of the magnetic sensing coils 20 when data is taken. That is, ferromagnetic cores and a potting compound having residual magnetism may be incorporated into the wand construction.

A block diagram of the control system 52 of the apparatus 10 is illustrated in FIG. 6. The transmitter 30, receivers 38 and wand receiver 48 are controlled by, and information received from, an electromagnetic system controller 54. The controller 54 and the wand receiver 48 are available commercially from Polhemus Navigation Sciences Division of McDonnell Douglas Electronics Company as the 3Space TM system. The required transmitter 30 and receivers 38, having substantially no residual magnetism, are specially constructed according to the descriptions presented above.

The controller 54 converts the electromagnetic signals received by the receivers 38 and the wand receiver 48 into six-axis location information for each of the receivers and the wand receiver. Six-axis location information includes three angular coordinates for the location of each receiver relative to the transmitter, plus three angular coordinates for the orientation in space of the receiver relative to the transmitter. To establish the exact location in space of each receiver 38 and the wand receiver 48, the six axis information for each receiving unit is obtained for each of the transmitters 30. When three receivers are used on the head of the patient, their positions may be determined using distance information and without the use of angular information, resulting in greater accuracy of the measurement. The resulting output of the controller 54 is a six-axis set of coordinates for each receiver 38 and the wand receiver 48, when the latter is activated. This location information is stored in the computer 26.

The biomagnetic data for the patient is received as an electrical signal from the sensors 20. The sensors 20 sense the very small magnetic fields attributable to the brain of the patient, and produce electrical signals. The electrical signals are furnished to a biomagnetic data controller 58, which amplifies the electrical signal and filters out signals of wavelengths that are known to be produced by external sources. The complexity of this electronic signal conditioning function is significantly reduced by providing the enclosure 28, which screens out spurious magnetic signals. The conditioned biomagnetic data signal is provided to the computer 26. The location information provided from the controller 54 and the biomagnetic data information provided from the controller 58 are correlated together in the computer 26.

Figure 7:
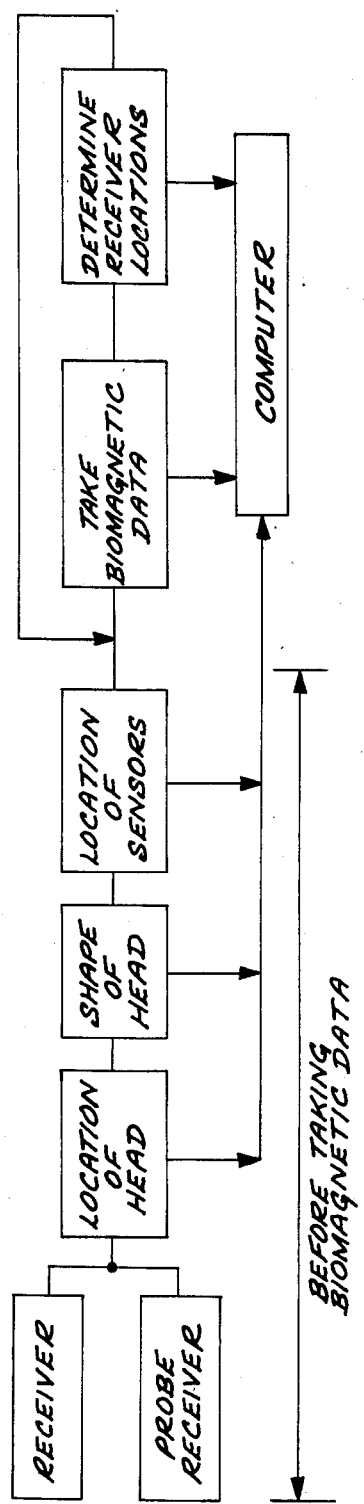
FIG. 7 is a block diagram of the process for making correlated biomagnetic and positional measurements.

Biomagnetic data correlated with the exact location of the head 14 is obtained by the process depicted in FIG. 7. Prior to commencing the taking of biomagnetic data, the location of the head 14 is determined relative to the receivers 38. With the receivers 38 operating to define their position relative to the transmitter 30, the wand receiver 48 is touched to reference points on the head 14. The locations of these reference points is thus determined relative to the receivers 38 for the duration of the data taking session. The locations of the reference points on the head 14 is determined from subsequent location measurements of the receivers 38, since the relative location of the reference points and the receivers 38 does not change during the data taking session, even though the relative position of the receivers 38 and the transmitter 30 may change.

Three reference points have been determined as preferred in establishing a head coordinate system, as illustrated in FIG. 2. Two are the left and right preauricular points 60. These points 60 are the soft indentations found just forward of the ear lobes. The other reference point is the nasion 62. The nasion 62 is the point between the eyes, where the upper side of the bridge of the nose meets the skull. There is no known special characteristic of these three points in regard to biomagnetic measurements, but they do provide convenient reference points when measurements are to be correlated with the location of the head. The reference points also are preferably used to define a head coordinate system to which all subsequent location measurements and biomagnetic data are correlated. The origin of the head coordinate system is defined as the point which is half way between the preauricular points.

Other reference points that can be relocated at a later time are also acceptable, such as a mole, birthmark, or mark placed on the head. As many reference points as is convenient may be defined, and normal practice is to define the locations of about five points at different positions on the head, so that three will be available regardless of the head position of the patient.

The shape of the head 14 is determined by operating the probe receiver 48 in a continuous position determining mode. The wand receiver 48 is drawn over the head of the patient in a number of tracks sufficient to define the head shape. Typically, about 20 traverses over the head define its shape, which is stored in the computer 56 in reference to the points 60 and 62, and the receivers 38. If desired, the head shape as stored in the computer memory can be displayed in real time, so that the person taking the measurements can visually determine when sufficient definition has been made.

Similarly, the locations of the magnetic field coils 20 relative to the transmitter 30 is determined by use of the probe receiver 48. The magnetic field coils 20 are contained within the dewars 22 and are therefore not visible. However, their location within the dewars 22 can be determined by careful measurements or by making an X-ray of the dewar 22 with the magnetic field coils 20 in place. These measurements define the location of the magnetic field coils with respect to reference marks on the external surface of the dewar 22. The locations of the magnetic field coils 20 are then defined by touching the probe receiver 48 to the reference marks on the exterior of the dewars 22, and correcting for the displacement of the sensors 20 from the reference marks.

The position of the head with respect to the magnetic sensing coils 20, the desired locational information, is determined as a vector sum of relative locations. The position of the head with respect to the transmitters 30 is determined using the wand receiver 48, with a simultaneous measurement of the position of the receivers 38, thereby providing the location of the head with respect to the receivers 38 as a vector. The position of the receivers 38 with respect to the transmitter 30 is measured during the course of the biomagnetic measurement session, yielding a vector position of the receivers with respect to the transmitter. The location of the magnetic field coils 20 is determined as the sum of a vector from the transmitter to the reference marks and a vector from the reference marks to the magnetic field coils 20. The location of the head with respect to the magnetic field coils 20 is therefore an appropriately added vector sum of the vector from the magnetic field coils to the reference marks (which is the negative of the vector of the reference marks to the magnetic field coils), plus the vector from the reference marks to the transmitter (which is the negative of the vector from the transmitter to the reference marks), plus the vector from the transmitter to the receivers, plus the vector from the receivers to the head coordinate system.

It is preferred that the procedure for obtaining locations be provided with sufficient redundancy that errors can be detected and minimized during the procedure. For example, the measurements of the preauricular points 60 and the nasion 62 can be repeated several times until there is no deviation, if the initial pair of determinations of each point indicates that there is an error, arising, for example, because the patient moves his head during this portion of the procedure. Multiple receivers are used to obtain multiple position vectors, due to the resiliency and shape variation of the head. The problem of obtaining the relative head location is more complex that that of obtaining the relative position of a rigid body of fixed, known shape. The use of three receivers, in the preferred embodiment, reduces errors due to the variations in head shape. Using three receivers, head positions can, at the present time, be determined to within about 2-3 millimeters accuracy.

The head positions as determined electromagnetically are stored in conjunction with the biomagnetic signal information for each of the magnetic field coils 20. The use of multiple coils 20 permits a three-dimensional map of magnetic field strength to be constructed. The magnetic field can then be correlated with the location within the head from which it originates. Particular portions of the brain are located separately, as by X-rays of the head, permitting a further correlation between the origin of the biomagnetic signals and the portions of the brain. Since it is known from other physiological studies that particular portions of the brain are correlated with certain activities, the present system permits correlations of biomagnetic signals with brain locations and functions, the medical objective of the study.

By the portion of the procedure completed before biomagnetic data is taken, the location of the head 14 is determined relative to the receivers 38. Should the patient move his head 14 during the later taking of biomagnetic data, the location of the head 14 can be almost continuously redetermined and correlated with the biomagnetic data from measurements of the locations of the receivers 38. Such movement of the patient is not uncommon. The position of the head can be redetermined by the electromagnetic technique of the invention in about 1/10 of a second, and can therefore be followed even during quick movements.

The biomagnetic data is taken continuously for a period of time and recorded in the computer. During the taking of biomagnetic data, the transmitter 30 and the receivers 38 may be inactive. Because they are constructed to have substantially no residual magnetism, there is substantially no spurious magnetic signal to interfere with the biomagnetic data. The wand receiver 48, having been used as necessary during the phase prior to the taking of data, is removed from the vicinity and has no effect on the data.

Biomagnetic data taking may continue or be discontinued during the determination of position. In the preferred approach, at selectable intervals the taking of biomagnetic data is discontinued, and the locations of the receivers 38 are determined by the technique previously described. Because a full determination typically requires only about 1/10 of a second, the taking of biomagnetic data is interrupted only very briefly. The locations are stored in the computer, and from this information the head locations and the head coordinate system can be determined at any time. The biomagnetic data is then correlated with the position of the head 14 in real time and stored for later evaluation.

Alternatively, taking of biomagnetic data can be continued during the determination of position. Biomagnetic data of interest in the range of DC to about 10 KHz. The transmitters 30 used to determine position can be operated at much higher frequencies, as about 25 KHz or higher. The signals of the transmitters 30 can therefore be effectively filtered from the biomagnetic data.

The present invention thus provides a system for taking biomagnetic data in which the data is readily correlated with the positions of the features of the head. The locations of the regions of the brain can be determined by X-ray or other technique and correlated to the reference points in a separate procedure. By matching the spatially correlated biomagnetic data and the biological locations of the regions of the brain, it is possible to locate the biological source of the magnetic fields to within about 2-3 millimeters, using the present approach.

Although a particular embodiment of the invention has been described in detail for purposes of illustration, various modifications may be made without departing from the spirit and scope of the invention. Accordingly, the invention is not to be limited except as by the appended claims.

What is claimed is:

1. Apparatus for making magnetic measurements of the human body, comprising:
   biomagnetometer means including a magnetic sensing coil for measuring magnetic fields arising form a selected portion of the body; and
   means for recording in real time the location of the selected portion of the body from which the magnetic fields emanate, said means for recording including electromagnetic means for sensing the location of the selected portion of the body using an electromagnetic signal, said electromagnetic means including a transmitter and a receiver of electromagnetic signals.

2. The apparatus of claim 1, wherein said biomagnetometer means includes a superconducting quantum interference device to measure the magnetic fields produced by the body.

3. The apparatus of claim 1, wherein the selected portion of the body is the head.

4. The apparatus of claim 1, wherein said electromagnetic means includes sending means for transmitting an electromagnetic signal through the air, and receiving means for receiving the transmitted electromagnetic signal, one of said sending means and said receiving means being mounted on the selected portion of the body and the other being mounted separated from the body.

5. The apparatus of claim 1, wherein said electromagnetic means includes at least two receiving units mounted on the selected portion of the body.

6. The apparatus of claim 1, wherein said electromagnetic means includes at least one receiving unit mounted on the selected portion of the body, said receiving unit having an antenna which receives electromagnetic signals in three axes.

7. The apparatus of claim 1, wherein said electromagnetic means includes sending means for transmitting an electromagnetic signal through the air, mounted on the body.

8. The apparatus of claim 1, wherein said electromagnetic means includes sending means for transmitting an electromagnetic signal through the air, mounted on said biomagnetometer means.

9. The apparatus of claim 1, wherein said electromagnetic means includes sending means for transmitting an electromagnetic signal through the air, mounted separately from the body and from said biomagnetometer means.

10. The apparatus of claim 1, wherein said electromagnetic means includes at least one receiving unit mounted on the selected portion of the body by an elastic band.

11. The apparatus of claim 1, further including a magnetically shielded room enclosing said biomagnetometer and the body being measured.

12. The apparatus of claim 1, wherein said electromagnetic means is constructed to have substantially no residual magnetism when not operating.

13. A process for obtaining biomagnetic data from the human body and correlating that data to the structure of the body, comprising the steps of:
   supplying apparatus according to claim 1;
   operating said means for recording intermittently to record the location of the selected portion of the body;
   taking data from said biomagnetometer means when said means for recording is not operating, thereby avoiding magnetic interference of the biomagnetic data from said means for recording; and
   recording the biomagnetic data with the information on the location of the selected portion of the body, whereby the biomagnetic data is correlated with the position of the body.

14. A process for obtaining biomagnetic data from the human body and correlating that data to the structure of the body, comprising the steps of:
   supplying apparatus according to claim 1;
   operating said means for recording conitnuously to record the location of the selected portion of the body, said means for recording operating at a frequency greater than about 10 KHz;
   taking data from said biomagnetometer means and filtering out signals having a frequency greater than about 10 KHz, thereby avoiding magnetic interference of the biomagnetic data from said means for recording; and recording the biomagnetic data with the information on the location of the selected portion of the body, whereby the biomagnetic data is correlated with the position of the body.

15. Apparatus for making magnetic measurements of the human body, comprising:
- a biomagnetometer including a sensor for measuring magnetic fields arising from a selected portion of the body;
- an elecromagnetic transmitter adjacent the body being measured, said transmitter having substantially no residual magnetism when no electric current is flowing therethrough;
- at least one electromagnetic receiver mounted on the selected part of the body, said electromagnetic receiver having substantially no residual magnetism when no electric current is flowing therethrough;
- an electromagnetic wand receiver that may be touched to points on the selected portion of the body to indicate the location of such points relative to said electromagnetic transmitter; and
- computer means for controlling and recording the locations of said receivers and said wand receiver, for taking data from said biomagnetometer, and for controlling said transmitter.

16. The apparatus of claim 15, wherein said receivers are mounted to the body by means of an elastic band.

17. The apparatus of claim 15, wherein said transmitter includes three orthogonal antennas, said antennas having no ferromagnetic cores therein.

18. The apparatus of claim 15, wherein said receivers include three orthogonal antennas, said antennas having no ferromagnetic cores therein.

19. The apparatus of claim 15, wherein said transmitter is potted in a nonmagnetic potting compound.

20. The apparatus of claim 15, wherein said receivers are potted in a nonmagnetic potting compound.

21. A process for obtaining biomagnetic data from the human body and correlating that data to the structure of the body, comprising the steps of:
- supplying apparatus according to claim 15;
- operating said transmitter and said receivers and said wand receiver intermittently to record the location of the selected portion of the body;
- taking data from said biomagnetometer when said transmitter, said receivers, and said wand receiver are not operating, thereby avoiding magnetic interference of the biomagnetic data from said transmitter, said receivers, and said wand receiver; and
- recording in said computer means the biomagnetic data with the information on the location of the selected portion of the body, whereby the biomagnetic data may be correlated with the location of the body.

22. The process of claim 21, wherein said step of operating includes the steps of:
- touching the wand receiver to selected reference points on the selected portion of the body with said transmitter on, to record the locations of said reference points with respect to said transmitter;
- operating the transmitter and said receivers to record the positions of said receivers with respect to said transmitter, thereby also correlating the positions of the reference points with respect to said receivers, whereby the locations of the reference points may be correlated with biomagnetic data taken from the selected portion of the body.

23. The processes of claim 21, wherein the selected portion of the body is the head, and the reference points are the left and right perauricular points and the nasion.

24. A process for obtaining biomagnetic data from the human body and correlating that data to the structure of the body, comprising the steps of:
- supplying apparatus according to claim 15;
- operating said transmitter and said receivers and said wand receiver continuously at a frequency greater than about 10 KHz to record the location of the selected portion of the body;
- taking data continuously from said biomagnetometer and filtering signals from said data having a frequency greater than about 10 KHz; and
- recording in said computer means the biomagnetic data with the information on the location of the selected portion of the body, whereby the biomagnetic data may be correlated with the location of the body.

* * * * *